US006355639B1

(12) United States Patent
Chou et al.

(10) Patent No.: US 6,355,639 B1
(45) Date of Patent: Mar. 12, 2002

(54) REVERSE PRENYL COMPOUNDS AS IMMUNOSUPPRESSANTS

(75) Inventors: Ting-Chao Chou, Paramus, NJ (US); Joseph R. Bertino, Branford, CT (US); Samuel J. Danishefsky, Englewood, NJ (US); Barry D. Kahan, Houston, TX (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/463,537
(22) PCT Filed: Sep. 18, 1998
(86) PCT No.: PCT/US98/19507
§ 371 Date: Feb. 16, 2000
§ 102(e) Date: Feb. 16, 2000
(87) PCT Pub. No.: WO99/15174
PCT Pub. Date: Apr. 1, 1999

Related U.S. Application Data
(60) Provisional application No. 60/059,504, filed on Sep. 22, 1997.

(51) Int. Cl.[7] .............................................. A61K 31/495
(52) U.S. Cl. ....................................................... 514/250
(58) Field of Search ......................................... 514/250

(56) References Cited

U.S. PATENT DOCUMENTS

| 5,284,947 A | 2/1994 | Kadam et al. ............... 544/245 |
| 5,338,845 A | 8/1994 | Barrow et al. ............... 544/343 |

FOREIGN PATENT DOCUMENTS

WO WO 97/18215 5/1997

OTHER PUBLICATIONS

Arai, et al., Structures of Fructigenines A and B, New Alkaloids Isolated from *Penicillium fructigenum* Takeuchi, *Chemical and Pharmaceutical Bulletin*, 37(11): 2937–2939, 1989.

Hino, et al., "Inverted Prenylation of $N_b$–Methoxycarbonyltryptamine, Synthesis of 3a–(1,1–Dimethylallyl)pyrrolo [2,3–b] indole and 1–(1,1–Dimethylallyl) tryptamine Derivatives", *Chem. Pharm. Bull.* 33(12): 5202–05, 1985.

Hochlowski, et al., "5–N–Acetylardeemin, A Novel Heterocyclic Compound Which Reverses Multiple Drug Resistance in Tumor Cells", II. Isolation and Elucidation of the Structure of 5–N–Acetylardeemin and Two Congeners, *The Journal of Antibiotics*, 46(3): 381–86, 1993.

Karwowski, et al., "5–N–Acetylardeemin, A Novel Heterocyclic Compound Which Reverses Multiple Drug Resistance in Tumor Cells", I. Taxonomy and Fermentation of the Producing Organism and Biological Activity, *The Journal of Antibiotics*, 46(3): 374–79, 1993.

Marsden, et al., "Stereoselective Totals Syntheses of Amauromine and 5–N–Acetylardeemin. A Concise Route to the Family of 'Reverse–Prenylated' Hexahydropyrroloindole Alkaloids", *J. Am. Chem.* 116: 11143–44, 1994.

(List continued on next page.)

*Primary Examiner*—Zohreh Fay
*Assistant Examiner*—C. Delacroix-Muirheid
(74) *Attorney, Agent, or Firm*—Karoline K. M. Shair; Choate, Hall & Stewart

(57) ABSTRACT

The present invention provides a method for treating a subject in need of immunosuppression, comprising administering to the subject an effective amount of a compound having structure (I) wherein $R_1$, $R_6$ and $R_7$ are independently hydrogen, OH, $NH_2$, SH, halogen, $C_1$–$C_9$ linear or branched chain alkyl, alkylmercapto, alkylamino, etc.; wherein $R_0$ and $R_2$ are independently hydrogen, OH, $C_1$–$C_9$ linear or branched chain alkyl, —$CR_3R_3$—$CH(O)CH_2$, —$CR_3R_3$—CH=$CHR_4$, etc.; wherein $R_3$ and $R_4$ are independently hydrogen halogen $C_1$–$C_9$ linear or branched chain alkyl, etc.; wherein $R_5$ is hydrogen, $C_1$–$C_9$ linear or branched chain alkyl, phenyl, alkylphenyl, dialkylphenyl, alkylmercapto, etc.; and wherein $R_8$ is hydrogen, $C_1$–$C_9$ linear or branched chain acyl, benzoyl, alkylbenzoyl, etc. Also provided are methods of treating autoimmune disease and preventing organ graft rejection using N-acetylardeemin and related compounds.

14 Claims, 6 Drawing Sheets

OTHER PUBLICATIONS

Parsons, et al., "Total Syntheses of Strychnan– and Aspidospermatan–Type Alkaloids, 2. Generation of 15–(3–Furanyl) ABCE Tetracyclic Intermediates", *J. Org. Chem.* 58: 7482–89, 1993.

Shinohara, et al., "Gypsetin, A New Inhibitor of Acyl–CoA: Cholesterol Acyltransferase Produced By *Nannizzia gypsea* Var. Incurvata IFO 9228. I. Fermentation, Isolation, Physico–Chemical Properties and Biological Activity", *The Journal of Antibiotics*, 47(2): 163–67, 1994.

Takase, et al., "Structure of Amauromine, A New Alkaloid with Vasodilating Activity Produced by Amauroascus Sp". *Tetrahedron*, 25(41): 4673–76, 1984.

Takase, et al., "Amauromine, A New Vasodilator Taxonomy, Isolation and Characterization", *The Journal of Antibiotics*, 37(11): 1320–23, 1984.

Takase, et al., "Total Synthesis of Amauromine", *Tetrahedron*, 42(21): 5887–94, 1986.

REVERSE PRENYL COMPOUNDS AS IMMUNOSUPPRESSANTS

This application is a Ser. No. 371 of PCT/US98/19507 filed Sep. 18, 1998 which claims benefit of Ser. No. 60/059,504 filed Sep. 22, 1997.

This invention was made with government support under grants AI-32350, CA-28824, CA-18856, HL-25848 and HL-09187 from the National Institutes of Health. Accordingly, the U.S. Government has certain rights in the invention.

FIELD OF THE INVENTION

This invention is in the field of clinical immunology, and relates to compounds having immunosuppressive properties. In particular, the invention relates to a method for treating immune disorders, including autoimmune or inflammatory diseases, and for reducing immunorejection of transplanted organs, said method comprising administering to a subject a therapeutically effective amount of N-acetylardeemin or an analog thereof.

BACKGROUND OF THE INVENTION

The immune system specifically recognizes and selectively eliminates foreign invaders, or other antigenic agents, by a process known as the immune response. Immune rejection is a major problem confronting organ transplantation. The principal approach to mitigate rejection is the pharmacological suppression of the immune system of an organ recipient. Immunosuppressive drugs are an important component in the prevention of organ graft rejection. Such drugs have been used to increase survival times for transplanted organs, including kidney, pancreas, liver, heart, intestines, lung, and bone marrow, allograft or autologous, either as single agents or in combination with other immunosuppresants. They are also useful for treating inflammatory diseases, delayed hypersensitivity, allergic encephalomyelitis and graft vs. host diseases.

Currently used immunosuppressive drugs include antiproliferative agents, such as methotrexate, azathioprine and cyclophosphamide. Since these drugs affect mitosis and cell division, they have severe toxic effects on normal cells with high turn-over rate such as bone marrow cells and the gastrointestinal tract lining. Marrow depression and liver damage are common side effects.

Antiinflammatory compounds used to induce immunosuppression include adrenal corticosteroids such as dexamethasone and prednisolone, and have the advantage of not generating systemic toxic effects. Since they are less specific, they are usually used together with antiproliferative agents. Among the common side effects observed with the use of these compounds are frequent infections, loss of hemodynamic balance and abnormal metabolism.

Other immunosuppresants in use are compounds which inhibit lymphocyte activation. Cyclosporin and its relatives are among the most commonly used immunosuppresants. Cyclosporin A is used for organ rejection in kidney, liver, heart, pancreas, bone-marrow and heart-lung transplants, as well as for the treatment of autoimmune and inflammatory diseases such as Crohn's disease, a plastic anemia, multiple-sclerosis, myasthenai gravis, uveitis, biliary cirrhosis, etc. However, cyclosporins can have severe toxic effects on various tissues, including the liver, kidney and nervous system.

Aside from organ or tissue transplant rejection, examples of immune system conditions or disorders which could benefit from treatment with an immunosuppressant agent include contact dermatitis; graft-vs-host disease in which donor immunological cells present in the graft attack host tissues in the recipient of the graft; diseases with proven or possible autoimmune components, such as rheumatoid arthritis, psoriasis, autoimmune uveitis, multiple sclerosis, allergic encephalomyelitis, systemic lupus erythematosis, aplastic anemia, pure red cell anemia, idiopathic thrombocytopenia, scleroderma, chronic active hepatitis, myasthenia gravis, Crohn's disease, ulcerative colitis, Graves ophthalmopathy, sarcoidosis, primary biliary cirrhosis, primary juvenile diabetes, uveitis posterior, and interstitial lung fibrosis.

Accordingly, in view of the ineffectiveness or toxicity of current therapeutic agents, an important clinical need exists for new selective, nontoxic immunosuppressive agents for use in organ transplantation, and in the treatment of autoimmune disorders.

SUMMARY OF THE INVENTION

One object of the present invention is to provide a method for suppressing pathogenic immune responses. In particular, an object of the invention is to provide a method for treating a subject in need of immunosuppression, comprising administering to the subject an effective amount of a compound having the structure:

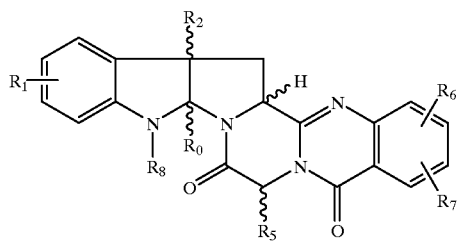

wherein $R_1$, $R_6$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, halophenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl, or $C_1$–$C_9$ linear or branched chain alkyl.

The invention also provides a method for preventing organ graft rejection in a subject in whom an organ has been transplanted, comprising administering to the subject an effective amount of a compound having the structure:

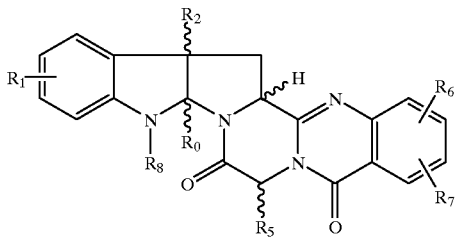

wherein $R_1$, $R_6$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, halophenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl, or $C_1$–$C_9$ linear or branched chain alkyl.

A further object of the invention is to provide a method for treating a subject suffering from an autoimmune disease, comprising administering to the subject an effective amount of a compound having the structure:

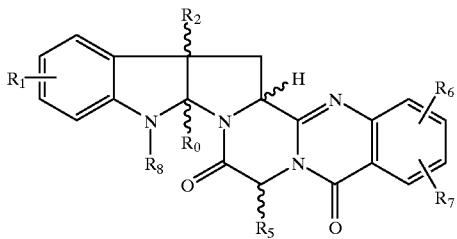

wherein $R_1$, $R_6$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, halophenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl, or $C_1$–$C_9$ linear or branched chain alkyl. subject in need of immunosuppression, comprising administering to the subject an effective amount of a compound having the structure:

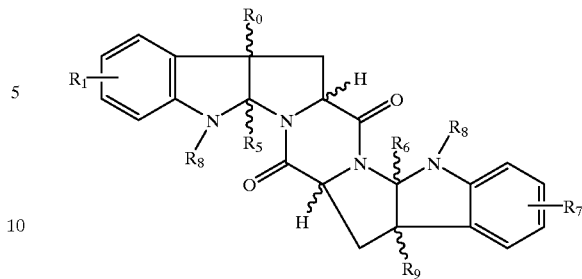

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_0$ and $R_5$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_6$ is hydrogen, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_7$ is hydrogen, halogen, $C_1$–$C_9$ linear or branched chain alkyl, alkylmercapto, alkylamino, dialkylamino, alkoxy, phenyl, alkylphenyl, dialkyl-phenyl, alkoxyphenyl, hydroxyphenyl or benzyl; wherein $R_8$ is $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; and wherein $R_9$ is hydrogen or OH.

A further object of the invention is to provide a method of preventing organ graft rejection in a subject in whom an organ has been transplanted, comprising administering to the subject an effective amount of a compound having the structure:

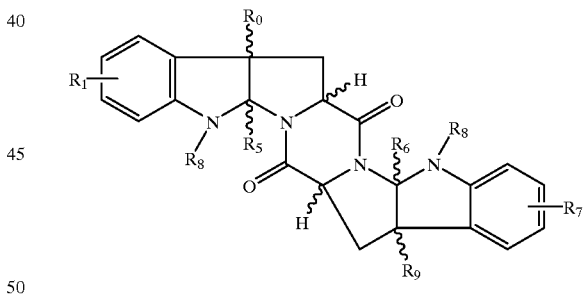

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_0$ and $R_5$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$CH=$CHR_4$; wherein $R_6$ is hydrogen, $CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_7$ is hydrogen, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_8$ is $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; and wherein $R_9$ is hydrogen or OH.

A further object of the invention is to provide a method of treating a subject suffering from an autoimmune disease, comprising administering to the subject an effective amount of a compound having the structure:

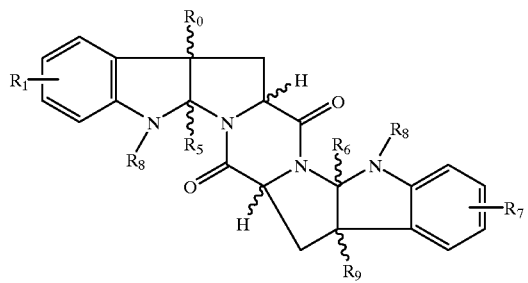

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_0$ and $R_5$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_6$ is hydrogen, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_7$ is hydrogen, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_8$ is $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; and wherein $R_9$ is hydrogen or OH.

An additional object of the invention is to provide a method for treating a subject in need of immunosuppression, comprising administering to the subject an effective amount of a compound having the structure:

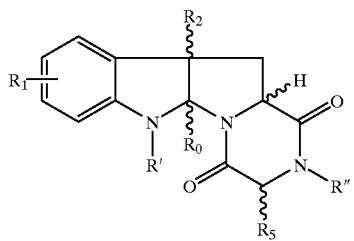

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein R' and R" are independently hydrogen, $C_1$–$C_9$ linear or branched chain alkyl, $C_1$–$C_9$ linear or branched chain acyl, benzoyl, alkylbenzoyl, dialkylbenzoyl, alkoxybenzoyl, or benzyl.

Another object of the invention is to provide a method for preventing organ graft rejection in a subject in whom an organ has been transplanted, comprising administering to the subject an effective amount of a compound having the structure:

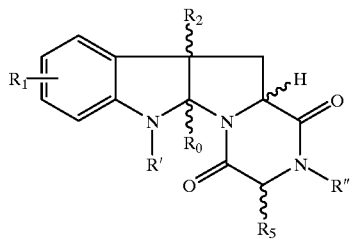

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein R' and R" are independently hydrogen, $C_1$–$C_9$ linear or branched chain alkyl, $C_1$–$C_9$ linear or branched chain acyl, benzoyl, alkylbenzoyl, dialkylbenzoyl, alkoxybenzoyl, or benzyl.

Another aspect of the invention is to provide a method for treating a subject suffering from an autoimmune disease, comprising administering to the subject an effective amount of a compound having the structure:

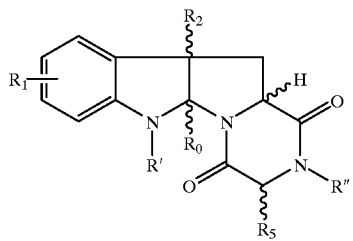

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein R' and R" are independently hydrogen, $C_1$–$C_9$ linear or branched chain alkyl, $C_1$–$C_9$ linear or branched chain acyl, benzoyl, alkylbenzoyl, dialkylbenzoyl, alkoxybenzoyl, or benzyl.

DETAILED DESCRIPTION OF THE INVENTION

Figure 1:
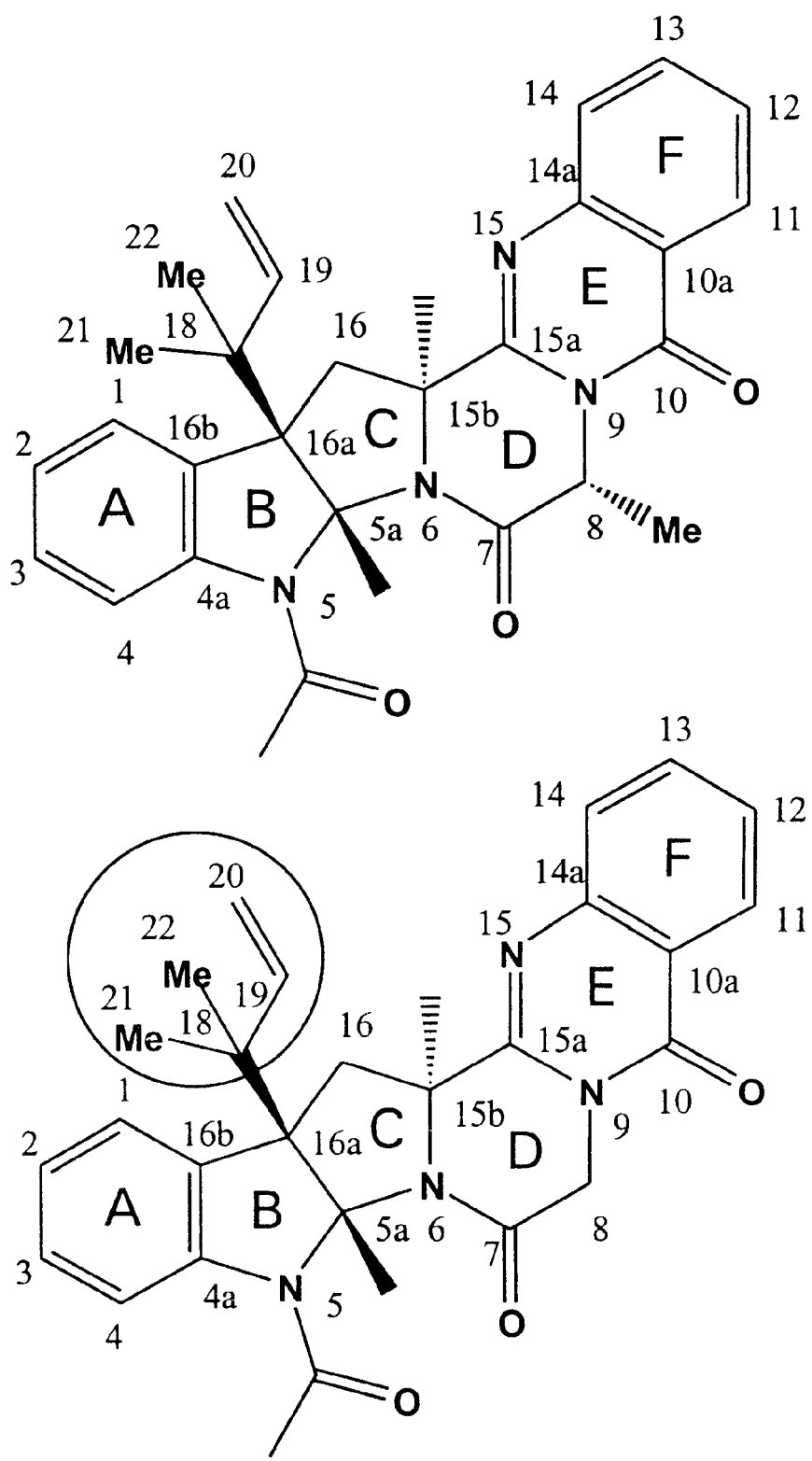
FIG. 1 illustrates the structures of 5-N-acetylardeemin (top) and 5-N-acetyl-8-desmethylardeemin.

The subject invention provides a method for treating a subject in need of immunosuppression, comprising administering to the subject an effective amount of a compound having the structure:

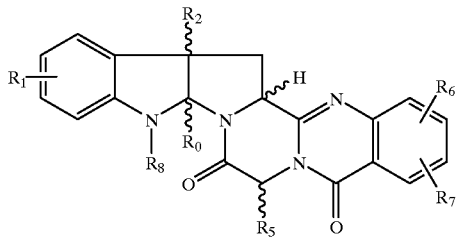

wherein $R_1$, $R_6$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, halophenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl, or $C_1$–$C_9$ linear or branched chain alkyl. In particular, the invention provides a method as disclosed wherein the compound has the structure:

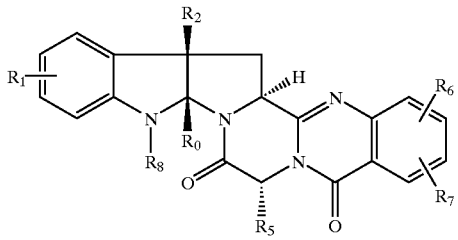

More particularly, the invention provides a method wherein $R_0$ is hydrogen. In addition, the method may be practiced using a compound wherein $R_0$, $R_1$, $R_3$, $R_4$, $R_6$, and $R_7$ are hydrogen; wherein $R_2$ is $CR_3R_3$—CH=$CHR_4$; wherein $R_5$ is H or $CH_3$; and wherein $R_8$ is —(C=O)$CH_3$.

The present invention also provides a method for preventing organ graft rejection in a subject in whom an organ has been transplanted, comprising administering to the subject an effective amount of a compound having the structure:

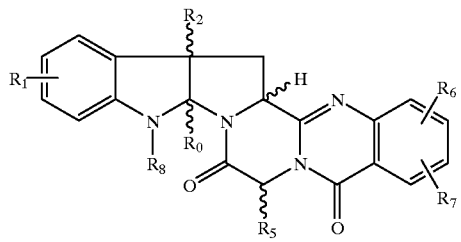

wherein $R_1$, $R_6$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, halophenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl, or $C_1$–$C_9$ linear or branched chain alkyl.

In one embodiment, the method is practiced wherein the compound has the structure:

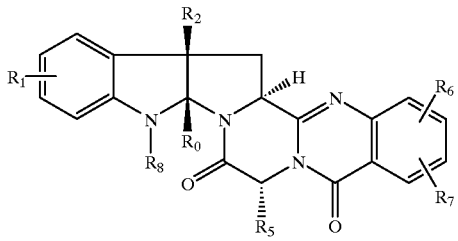

In particular, $R_0$ may be hydrogen. More particularly, the method of the invention is practiced using the compound wherein $R_0$, $R_1$, $R_3$, $R_4$, $R_6$, and $R_7$ are hydrogen; wherein $R_2$ is $CR_3R_3$—CH=CHR$_4$; wherein $R_5$ is H or CH$_3$; and wherein $R_5$ is H or CH$_3$; and wherein $R_8$ is —(C=O)CH$_3$. In a certain embodiment, the method is applied wherein the organ is kidney, pancreas, liver, heart or bone marrow.

The present invention further provides a method for treating a subject suffering from an autoimmune disease, comprising administering to the subject an effective amount of a compound having the structure:

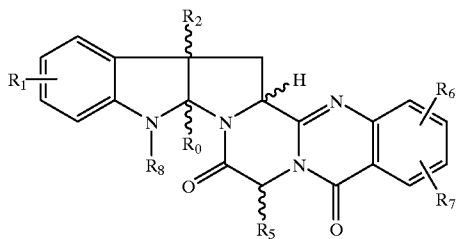

wherein $R_1$, $R_6$ and $R_7$ are independently hydrogen, OH, NH$_2$, SH, halogen, $C_1$–$C_9$ linear or branched chain alkyl, alkylmercapto, alkylamino, dialkylamino, alkoxy, phenyl, alkylphenyl, dialkylphenyl, halophenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —CR$_3$R$_3$—CH(O)CH$_2$, —CR$_3$R$_3$—CH$_2$CH$_3$, —CR$_3$R$_3$—CH$_2$CH$_2$OH, —CR$_3$R$_3$—CH(OH)R$_4$ —CR$_3$R$_3$—CH=CHR$_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl, or $C_1$–$C_9$ linear or branched chain alkyl. In one embodiment, the invention provides the method as disclosed wherein the compound has the structure:

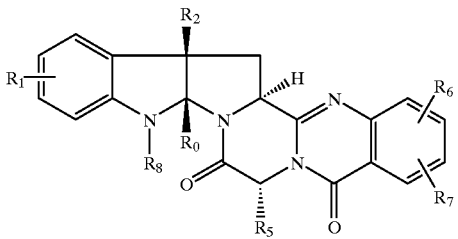

In a certain embodiment, the method is practiced using a compound wherein $R_0$ is hydrogen. In certain other embodiments, the method is practiced wherein $R_0$, $R_1$, $R_3$, $R_4$, $R_6$, and $R_7$ are hydrogen; wherein $R_2$ is $CR_3R_3$—CH=CHR$_4$; wherein $R_5$ is H or CH$_3$; and wherein $R_8$ is —(C=O)CH$_3$. The method is particularly applicable wherein the disease is multiple sclerosis, rheumatoid arthritis, Crohn's disease or aplastic anemia.

A method for treating a subject in need of immunosuppression, comprising administering to the subject an effective amount of a compound having the structure:

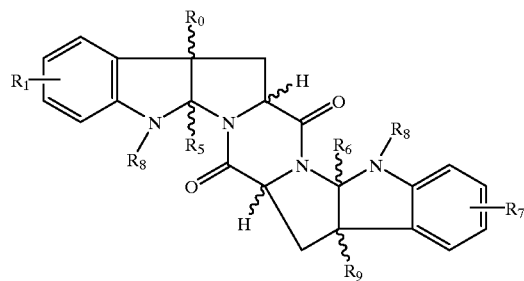

wherein $R_1$ is hydrogen, OH, NH$_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_0$ and $R_5$ are independently hydrogen, OH, $C_1$–$C_9$ linear or branched chain alkyl, —CR$_3$R$_3$—CH(O)CH$_2$, —CR$_3$R$_3$—CH$_2$CH$_3$, —CR$_3$R$_3$—CH$_2$CH$_2$OH, —CR$_3$R$_3$—CH(OH)R$_4$ or —CR$_3$R$_3$—CH=CHR$_4$; wherein $R_6$ is hydrogen, —CR$_3$R$_3$—CH(O)CH$_2$, —CR$_3$R$_3$—CH$_2$CH$_3$, —CR$_3$R$_3$—CH$_2$CH$_2$OH, —CR$_3$R$_3$—CH(OH)R$_4$ or —CR$_3$R$_3$—CH=CHR$_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_7$ is hydrogen, halogen, $C_1$–$C_9$ linear or branched chain alkyl, alkylmercapto, alkylamino, dialkylamino, alkoxy, phenyl, alkylphenyl, dialkyl-phenyl, alkoxyphenyl, hydroxyphenyl or benzyl; wherein $R_8$ is $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; and wherein $R_9$ is hydrogen or OH. In one embodiment, the invention provides the method wherein the compound has the structure:

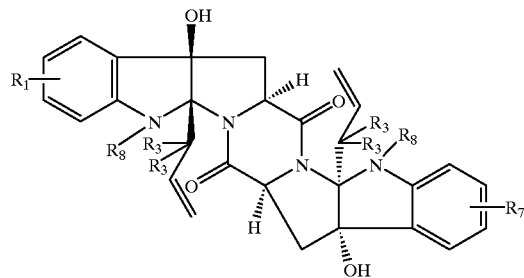

The present invention also provides a method of preventing organ graft rejection in a subject in whom an organ has been transplanted, comprising administering to the subject an effective amount of a compound having the structure:

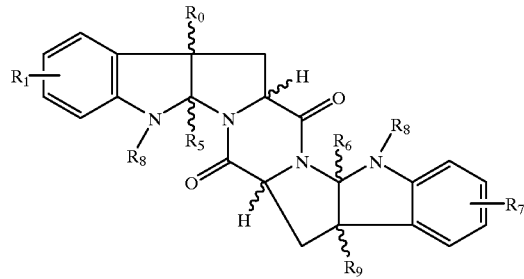

wherein $R_1$ is hydrogen, OH, NH$_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_0$ and $R_5$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—$CH(OH)R_4$ or —$CR_3R_3$—CH=$CHR_4$; wherein $R_6$ is hydrogen, $CR_3R_3$—CH(O)$CH_2$, —$CR_3R_3$—$CH_2CH_3$, —$CR_3R_3$—$CH_2CH_2OH$, —$CR_3R_3$—$CH(OH)R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_7$ is hydrogen, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_8$ is $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; and wherein $R_9$ is hydrogen or OH. In one embodiment, the compound has the structure:

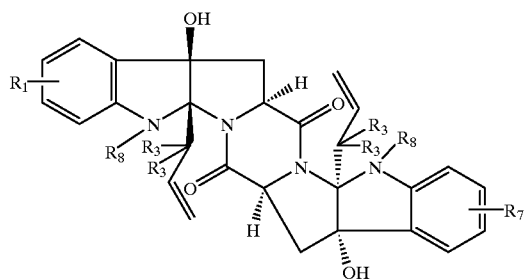

In particular, the method may be practiced wherein the organ is kidney, pancreas, liver, heart or bone marrow.

The present invention further provides a method of treating a subject suffering from an autoimmune disease, comprising administering to the subject an effective amount of a compound having the structure:

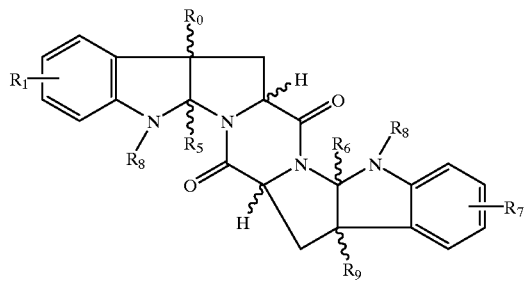

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_0$ and $R_5$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—$CH(OH)R_4$ or —$CR_3R_3$—CH=$CHR_4$; wherein $R_6$ is hydrogen, —$CR_3R_3$—CH(O)$CH_2$, —$CR_3R_3$—$CH_2CH_3$, —$CR_3R_3$—$CH_2CH_2OH$, —$CR_3R_3$—$CH(OH)R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl or benzyl; wherein $R_7$ is hydrogen, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl or benzyl; wherein $R_8$ is $C_1$–$C_9$ linear or branched chain acyl, benzoyl, alkylbenzoyl, dialkylbenzoyl, alkoxybenzoyl, benzyl or $C_1$–$C_9$ linear or branched chain alkyl; and wherein $R_9$ is hydrogen or OH. In one embodiment, the compound has the structure:

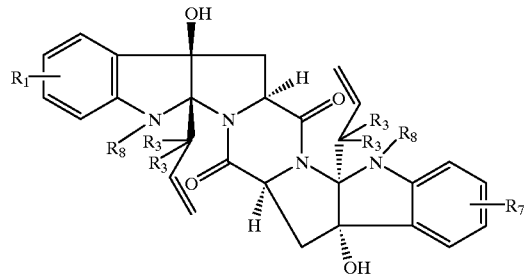

The method may be practiced wherein the disease is multiple sclerosis, rheumatoid arthritis, Crohn's disease or aplastic anemia.

The present invention also provides a method for treating a subject in need of immunosuppression, comprising administering to the subject an effective amount of a compound having the structure:

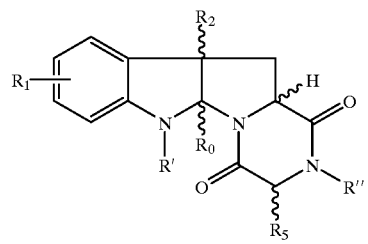

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—$CH(OH)R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein R' and R" are independently hydrogen, $C_1$–$C_9$ linear or branched chain alkyl, $C_1$–$C_9$ linear or branched chain acyl, benzoyl, alkylbenzoyl, dialkylbenzoyl, alkoxybenzoyl, or benzyl. In a certain embodiment, the compound has the structure:

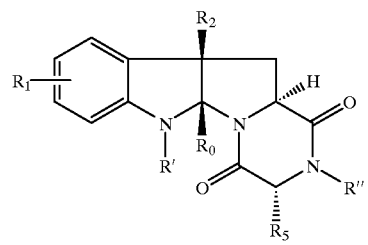

The present invention also provides a method for preventing organ graft rejection in a subject in whom an organ has been transplanted, comprising administering to the subject an effective amount of a compound having the structure:

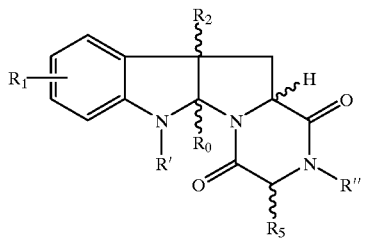

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=CH$R_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein R' and R" are independently hydrogen, $C_1$–$C_9$ linear or branched chain alkyl, $C_1$–$C_9$ linear or branched chain acyl, benzoyl, alkylbenzoyl, dialkylbenzoyl, alkoxybenzoyl, or benzyl. In a certain embodiment, the compound has the structure:

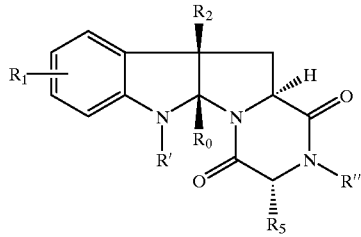

In particular, the method is practiced wherein the organ is kidney, pancreas, liver, heart or bone marrow.

The present invention provides a method for treating a subject suffering from an autoimmune disease, comprising administering to the subject an effective amount of a compound having the structure:

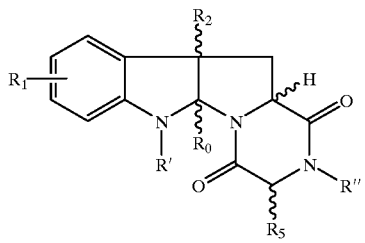

wherein $R_1$ is hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=CH$R_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein R' and R" are independently hydrogen, $C_1$–$C_9$ linear or branched chain alkyl, $C_1$–$C_9$ linear or branched chain acyl, benzoyl, alkylbenzoyl, dialkylbenzoyl, alkoxybenzoyl, or benzyl. In a certain embodiment, the compound has the structure:

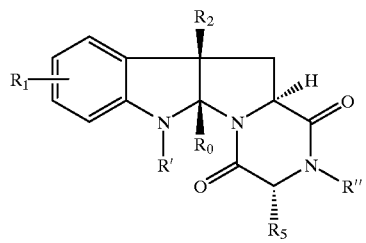

The method may be practiced wherein the disease is multiple sclerosis, rheumatoid arthritis, Crohn's disease or aplastic anemia.

In accord with the method of the present invention, ardeemin analogues are useful in treating subjects in need of immunosuppression, both in vivo and in vitro. The ability of these compounds to induce immunosuppression in cells, as demonstrated by the data disclosed below, shows that ardeemin analogues are useful to treat subjects in need of immunosuppression. In addition, mammals, and specifically humans, suffering from pathogenic immune responses can be treated by administering to the subject an effective amount of an ardeemin analogue in the presence of a pharmaceutically acceptable carrier or diluent. For example, the compounds of the invention may be administered to a subject to reduce or suppress an immune response, as that of an autoimmune disease. Examples of autoimmune diseases amenable to treatment by the method of the present invention include: Crohn's disease, rheumatoid arthritis, multiple sclerosis, myasthenia gravis, aplastic anemia, cirrhosis, red cell aplasia, diabetes mellitus, nephrotic syndrome and amyotrophic lateral sclerosis. In addition, the method of the present invention is useful in the prophylaxis of organ rejection and the treatment of organ graft rejection. Ardeemin compounds disclosed herein may be administered periodically to a subject who has undergone bone marrow transplantation or organ transplantation. For any of these purposes, it may be advantageous to combine an ardeemin compound with another immunosuppressant agent, such as cyclosporin, FK-506, 15-deoxyspergualin, rapamycin, etc. The precise amount of such additional agent may be determined as described below for the ardeemin compounds.

Also embraced within this invention is a class of pharmaceutical compositions comprising one or more ardeemin compounds disclosed herein with one or more non-toxic, pharmaceutically-acceptable carriers and/or diluents and/or adjuvants (collectively referred to herein as "carrier" materials) and, if desired, other active ingredients. The compounds of the present invention may be administered to a mammalian subject, such as a human subject, by any suitable route, preferably in the form of a pharmaceutical composition adapted to such a route, and in a dose effective for the treatment intended. Therapeutically-effective doses of the ardeemin compounds of the present invention required to prevent or arrest the progress of the medical condition are readily ascertained by one of ordinary skill in the art.

The compounds and compositions of ardeemin analogues used in the disclosed method include compositions suitable for oral, rectal, topical (including transdermal devices, aerosols, creams, ointments, lotions and dusting powders), parenteral (including subcutaneous, intramuscular and intravenous), ocular (ophthalmic), pulmonary (nasal or buccal inhalation) or nasal administration. Although the most suitable route in any given case will depend largely on the nature and severity of the condition being treated and on the nature of the active ingredient. They may be conveniently presented in unit dosage form and prepared by any of the methods well known in the art of pharmacy. A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents and adjuvant materials can be included as part of the composition.

In preparing oral dosage forms, any of the unusual pharmaceutical media may be used, such as water, glycols, oils, alcohols, flavoring agents, preservatives, coloring agents, and the like in the case of oral liquid preparations (e.g., suspensions, elixirs and solutions); or carriers such as starches, sugars, microcrystalline cellulose, diluents, granulating agents, lubricants, binders, disintegrating agents, etc., in the case of oral solid preparations are preferred over liquid oral preparations such as powders, capsules and tablets. If desired, capsules may be coated by standard aqueous or non-aqueous techniques.

In a preferred form of administration, the ardeemin analogue is prepared with carriers which guard against rapid elimination from the body, such as a controlled-release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations are known to those skilled in the art. Liposomal suspensions are particularly useful as carriers. These are prepared by methods known in the art, as, for example, in U.S. Pat. No. 4,522,811. Liposome formulations are prepared by dissolving one or more lipids (such as stearoyl phosphatidyl ethanolamine, stearoyl phosphatidyl choline, arachadoyl phosphatidyl choline, and cholesterol) in an organic solvent. On evaporation, a thin film of dried lipid remains. An aqueous solution of the N-acetylardeemin analogue is then added. After swirling to free lipid material from the sides of the container and to disperse lipid aggregates, the liposomal drug suspension results.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the ardeemin compounds and/or compositions of this invention is selected in accordance with a variety of factors, including the type, age, weight, sex and medical condition of the patient, the severity of the disease, the route of administration, and the particular compound employed, and thus may vary widely.

The present invention will be better understood from the Experimental Details which follow. However, one skilled in the art will readily appreciate that the specific methods and results discussed are merely illustrative of the invention as described in the claims which follow thereafter.

EXPERIMENTAL DETAILS

Materials

The analogues of ardeemin used in carrying out the immunosuppressive methods disclosed herein are prepared by synthetic procedures disclosed in U.S. Ser. No. 08/749,908, filed Nov. 15, 1996, which was based on U.S. Ser. No. 60/006,750, filed Nov. 15, 1995, the contents of which are incorporated herein by reference. If a primary, secondary or tertiary amine is in the free amine form, the ardeemin analogue may be provided in the form of a pharmaceutically-acceptable acid addition salt. As used herein, the term "pharmaceutically-acceptable salt" includes such salts as salts formed from such inorganic acids as hydrochloric acid, hydrobromic acid, sulfuric acid, phosphoric acid, nitric acid, etc., and salts formed from such organic acids as acetic acid, tartaric acid, succinic acid, malic acid, ascorbic acid, benzoic acid, methanesulfonic acid, tannic acid, etc. If a carboxylic acid or sulfonic acid group is present, the ardeemin analogue may be provided as a metal salt. Examples include salts formed from such metal cations as magnesium, calcium, zinc, bismuth, barium, aluminum, etc.

EXAMPLE 1

Inhibitory Effects of Ardeemin Compounds on the Activation of Human Peripheral Blood Lymphocytes by Phytohemagglutinin Thymidine Incorporation Assay:

PBL were exposed to various concentrations of drugs for 30 min and then added 10 μg/ml PHA for 24 hrs. [$^3$H]Thd (1 μCi/well) was then added and incubated for 1 hr. The reaction is stopped by adding 10% TCA for analysis of [$^3$H]Tdk incorporation into DNA.

Figure 2A:
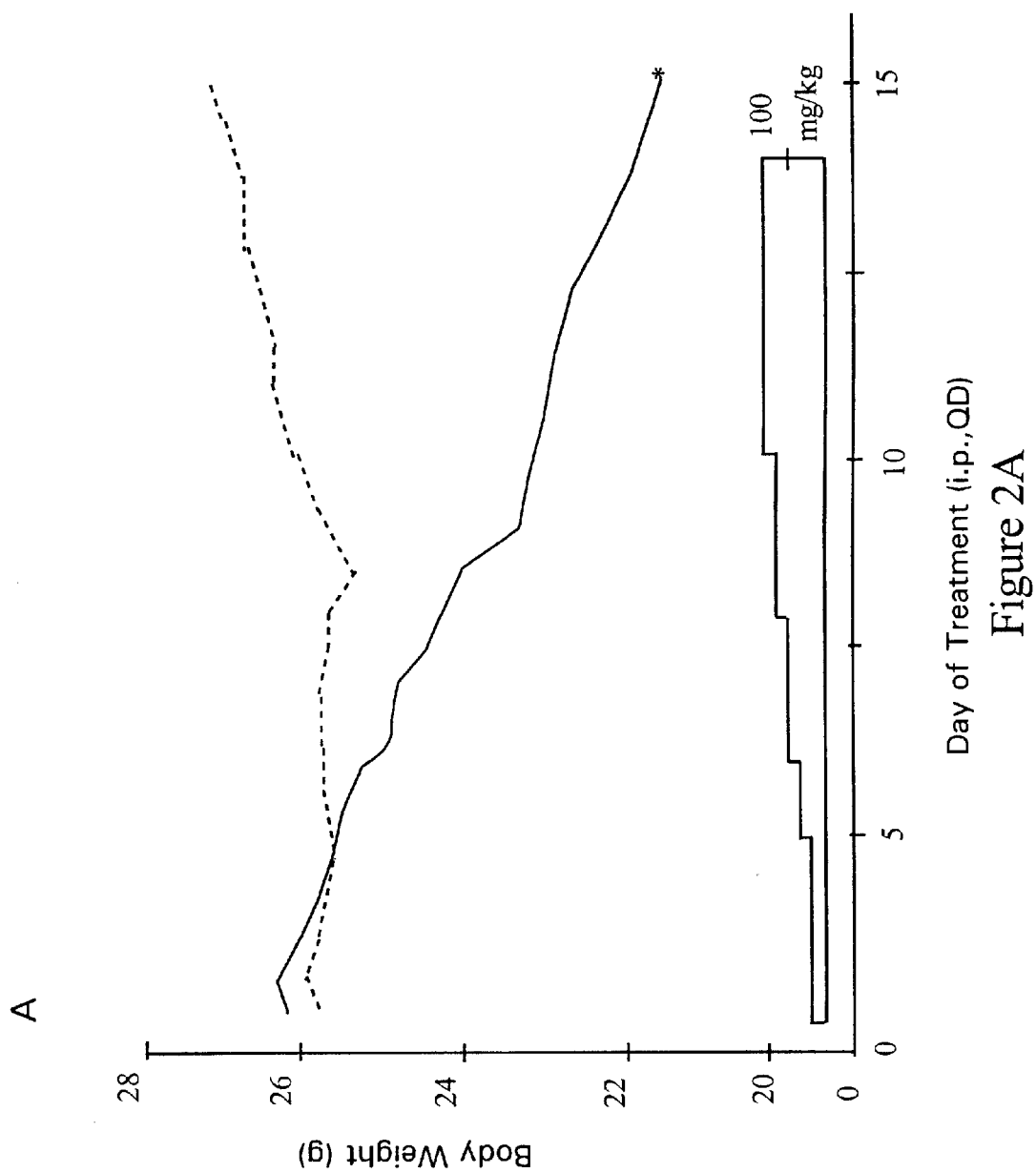
FIG. 2 illustrates the cumulative toxicity in $B_6D_2F_1$ mice treated with multidrug resistance reversal agents (mg/kg, i.p.,QD). Each group consists of five mice. All groups survived except for the verapamil-treated group wherein two of the five mice died. Cumulated doses in the series shown in panels A, B and C were 712.5, 1700 and 3950 mg/kg×day, respectively.
Figure 2B:
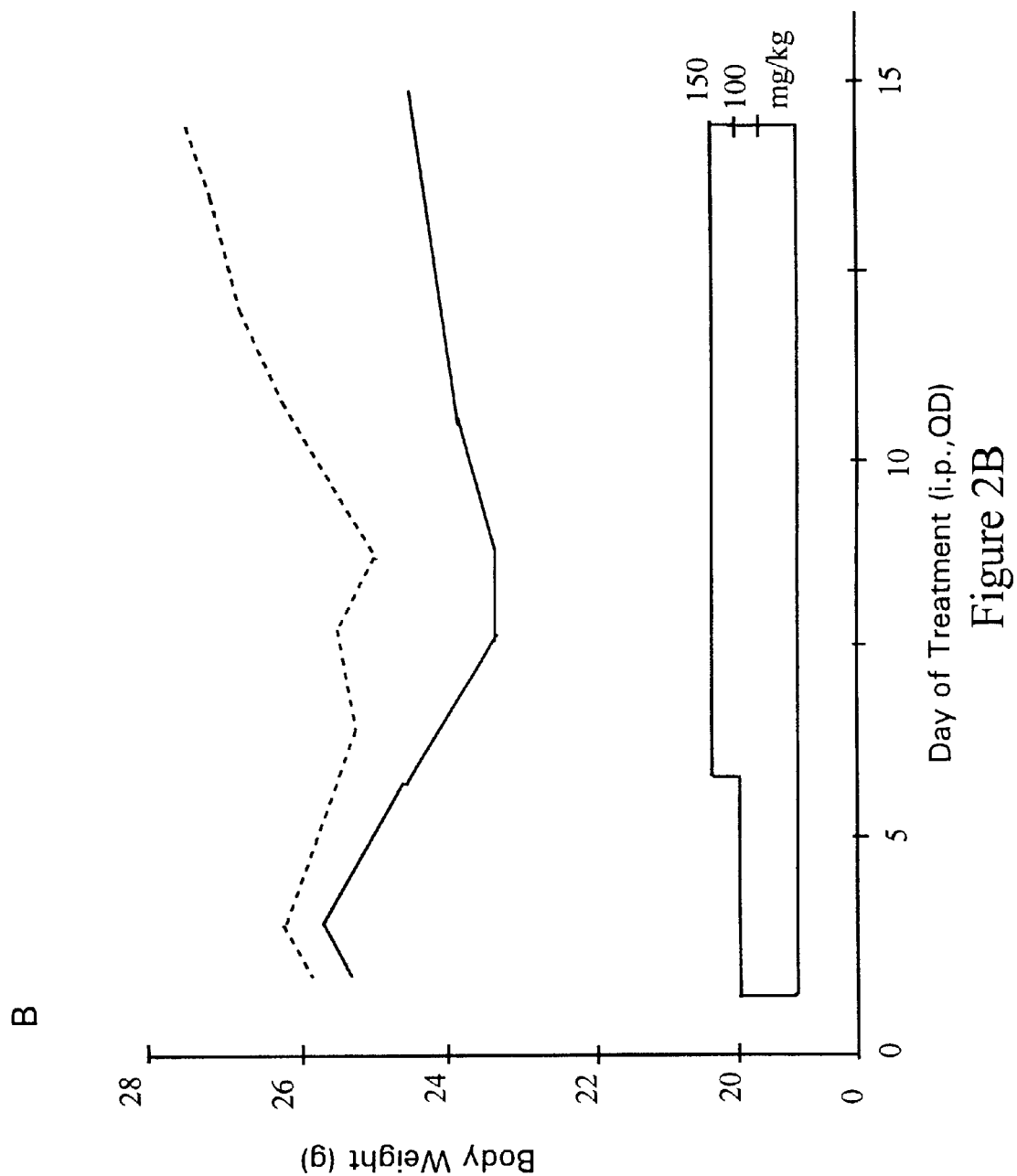
Figure 2C:
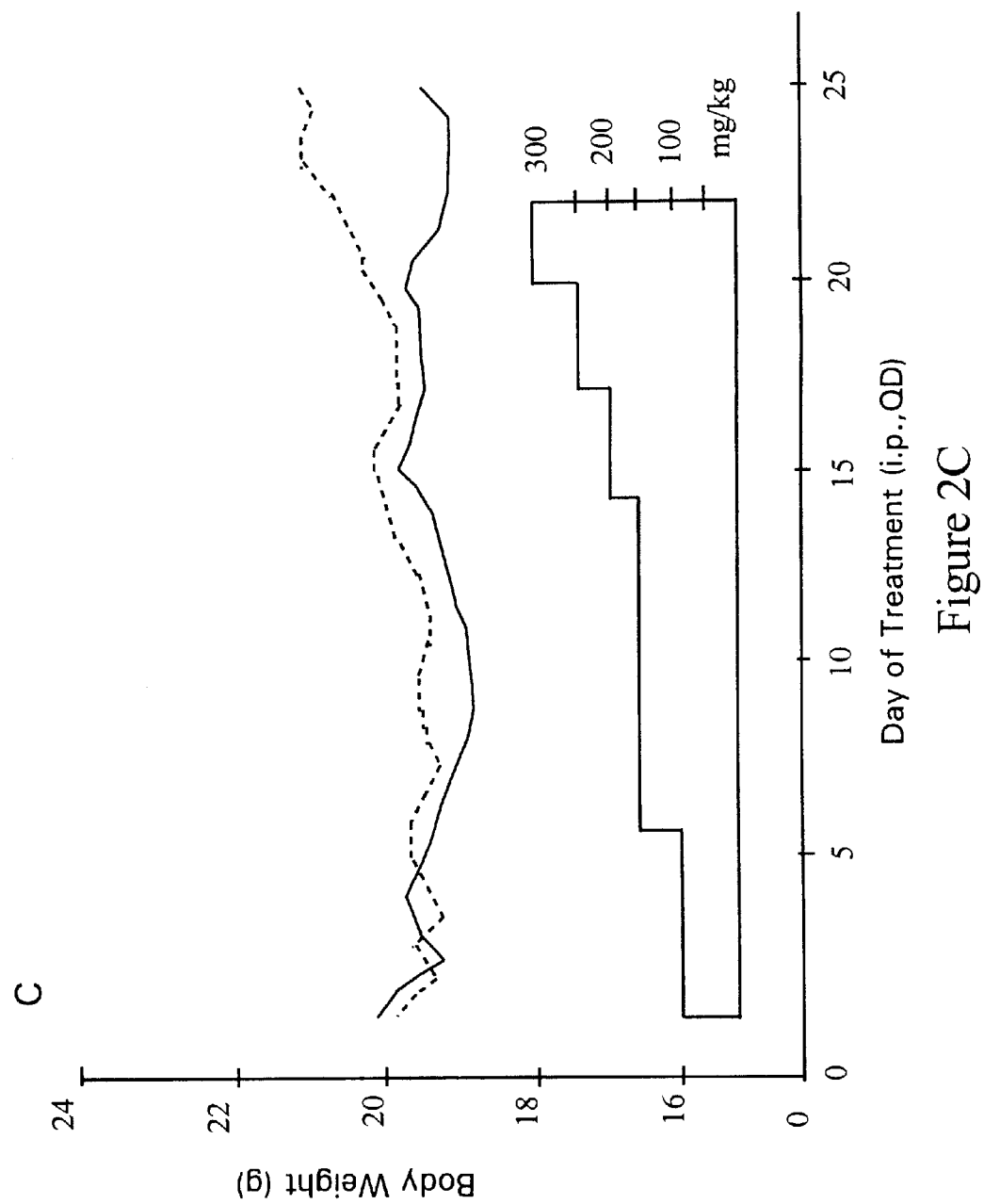
Figure 3:
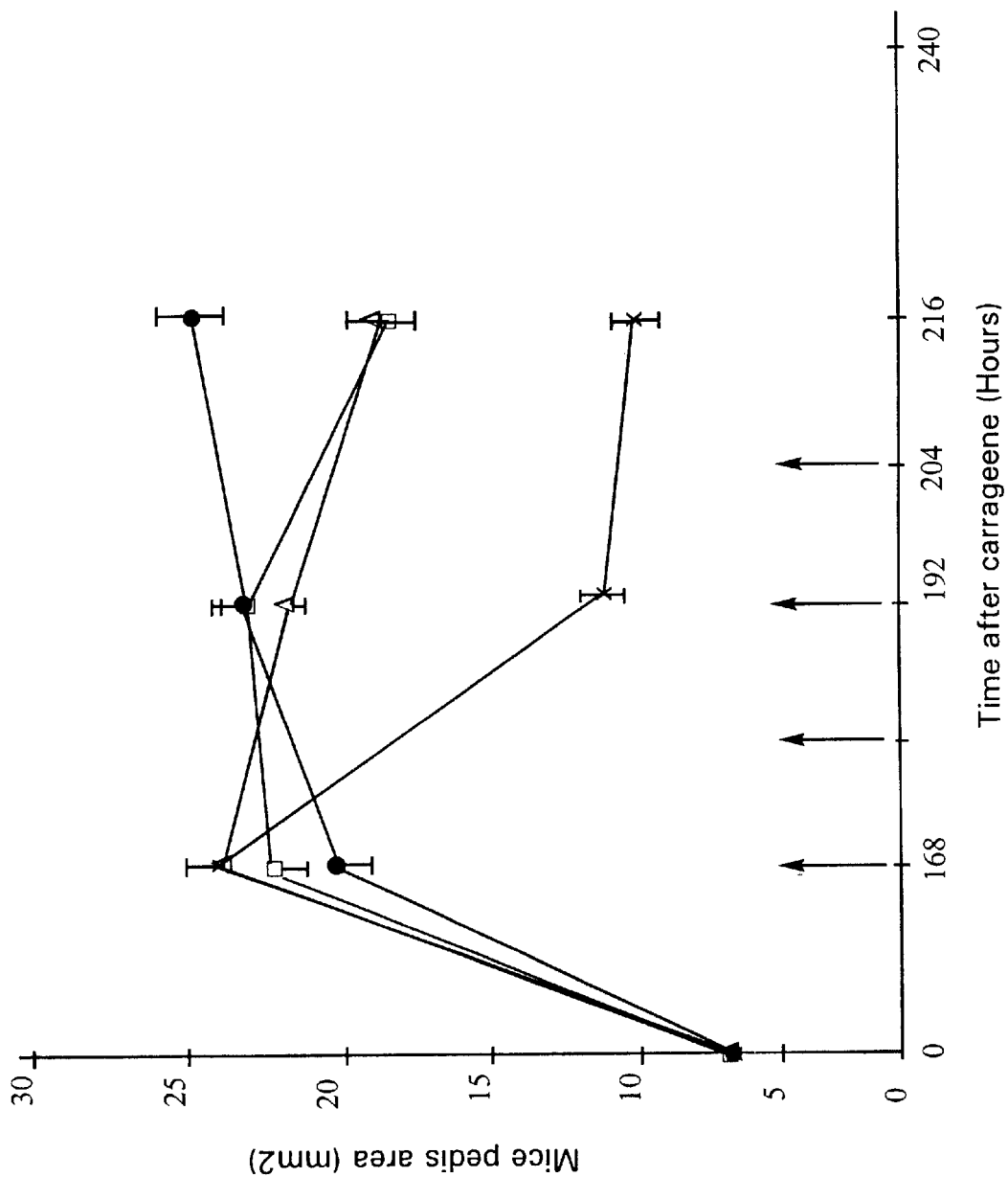
FIG. 3 illustrates the delayed treatment of inflammation induced by carrageene with aspirin, N-acetylardeemin and hydrocortisone. (●) Control; (■) Aspirin (500 mg/kg, p.o.); (Δ) N-acetylardeemin (100 mg/kg, i.p.); (x) Hydrocortisone cream.
Figure 4:
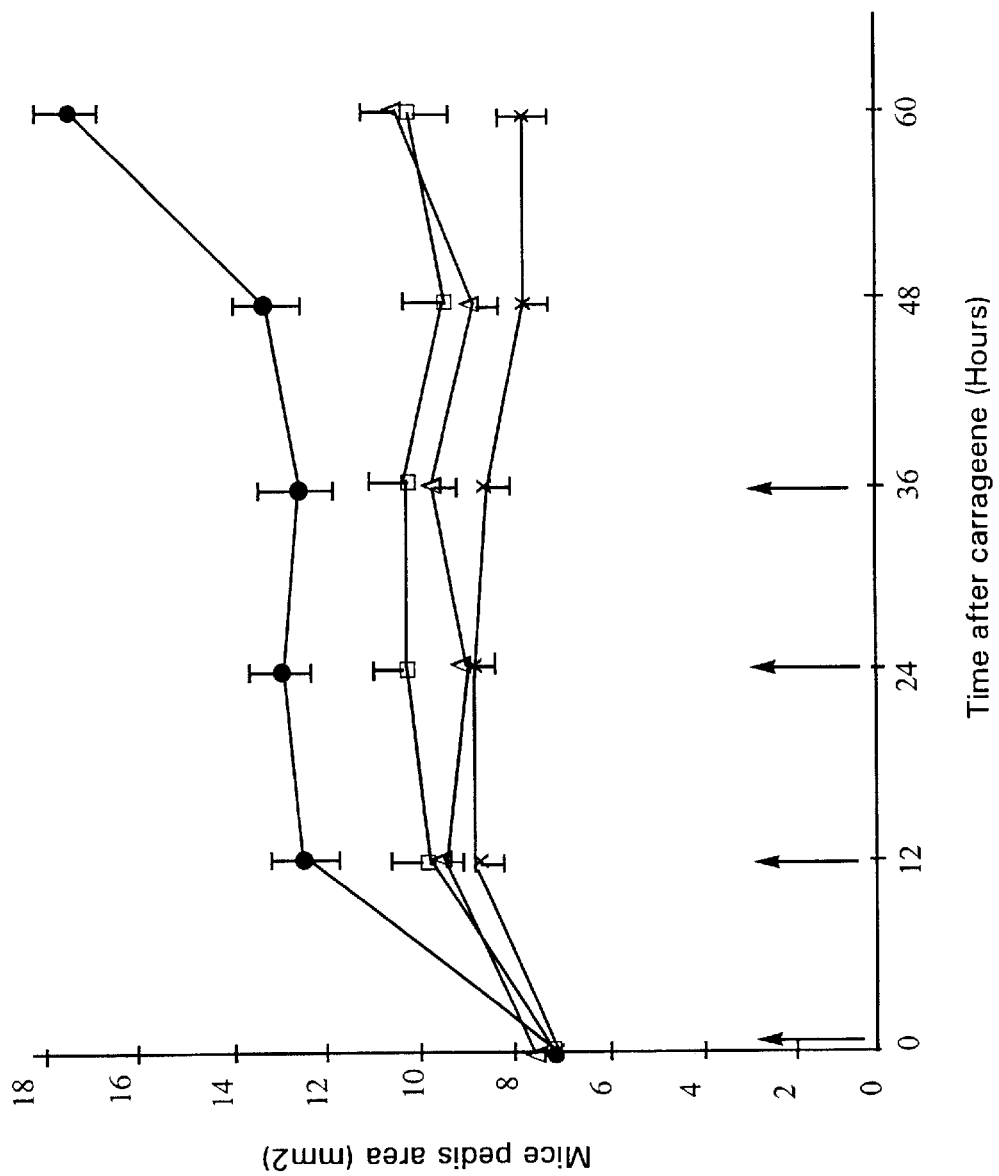
FIG. 4 illustrates the treatment of inflammation induced by carrageene with aspirin, N-acetylardeemin and hydrocortisone. (●) Control; (■) Aspirin (500 mg/kg, p.o.); (Δ) N-acetylardeemin (100 mg/kg, i.p.); (x) Hydrocortisone cream.

Results are tabulated in Table 1. As shown therein, ardeemin analogues are effective immunosuppresants in lymphocyte activation experiments in vitro. They are slightly less active than cyclosporine A or rapamycin but more active than brequinard or dexamethasone. It should be noted, however, that 5N-Ac-Ard is relatively nontoxic and 5-NAc-8-desmethyl ardeemin is very nontoxic to mice (see FIG. 2).

TABLE 1

Inhibitory Effects of Ardeemin Compounds on the Activation of Human Peripheral Blood Lymphocytes by Phytohemagglutinin

| Compound | $IC_{50}(\mu M)$ |
|---|---|
| Ardeemin Compounds | |
| 5-N-acetylardeemin | 1.91 |
| 8-demethylardeemin | 2.26 |
| 5-N-acetyl-8-demethyl-ardeemin | 0.98 |
| (Established immuno-suppressive Agents) | |
| Cyclosporine A | 0.15 |
| Rapamycine | 0.61 |
| Brequinard | 11.2 |
| Dexamethasone | 28.2 |

EXAMPLE 2

Immunosuppressive Effects of Ardeemin Derivatives in PHA and $OKT_3$ Stimulation Assays Fresh peripheral blood lymphocytes isolated by Ficoll-Hypaque density centrifugation are stimulated by PHA or the $OKT_3$ antibody (anti-CD3), which stimulates via interaction with CD3. Stimulation is measured by incorporation of radioactive thymidine [($^3$H)TdR] into proliferating cells, with an unhibited control signal of 48,000–75,000 cpm. $IC_{50}$ values are estimated from inhibitions of proliferation observed at various drug concentrations.

Results are presented in Table 2. It is evident that five of six reverse prenyl (ardeemin) compounds showed potent immunosuppressive effects. Notably, 5-N-acetyl-8-desmethylardeemin and 8-desmethylardeemin exhibit immunosuppressive $IC_{50}$ values of between 1.2–2.3 $\mu M$ in both assays. 5-N-acetyl-8-desmethylardeemin was found to be non-toxic to mice with sequential treatments at 100 mg/kg i.p., QDx6→150 mg/kg QDx8→200 mg/kg, QDx3→300 mg/kg, QDx3. Up to 250 mg/kg, Qdx3, the average body weight decreases were less than 0.5 g.

TABLE 2

IC$_{50}$ Values for immunosuppressants in PHA and OKT$_3$ Stimulation Assays

| | $IC_{50}$ ($\mu M$) | |
|---|---|---|
| Compound | PHA Assays | OKT$_3$ Assays |
| Classical immunosuppressant (historical data) | | |
| Cyclosporin A | 0.19 ± 0.05 | 0.05 ± 0.018 |
| Rapamycin | 0.61 ± 0.32 | 0.14 ± 0.08 |
| FK-506 | 0.029 ± 0.008 | 0.027 ± 0.020 |
| Brequinard | 11.2 ± 4.0 | 56.6 ± 22.7 |
| MPA | 0.095 ± 0.027 | 0.416 ± 0.210 |
| 6-MP | 0.044 ± 0.017 | 0.136 ± 0.019 |
| Reverse Prenyl Compounds | | |
| Gypsetin | 5.48 ± 1.24 | 11.97 ± 0.51 |
| 5-N-Ac-Ardeemin | 7.96 | 31.9 |
| 5-N-Ac-8-desmethylardeemin | 1.2 ± 0.02 | 1.13 ± 0.13 |
| 8-Desmethylardeemin | 2.26 ± 0.06 | 2.23 ± 0.16 |
| 5-N-Ac-F$_3$-Ardeemin | 9.97 ± 1.49 | 4.56 |
| 5-N-Ac-F$_3$-Diketopiperazine | >50 | >50 |

EXAMPLE 3

Lifespan Reduction of Tumor-Bearing Mice

Survival times were determined for $B_6D_2F_1$ mice inoculated with P388/0 cells, $10^6$ cells/mouse, i.p. at Day 0. The mice were treated by adriamycin and 5-N-acetylardeemin, i.p., daily for four days. Survival times were recorded based on the time of death with the following scheme of decimal values: 8AM (0.0), 1PM (0.25), 5PM (0.5). Results are tabulated in Table 3. An in vivo immunosuppressive effect of the ardeemin derivatives is found which persistently shortens the lifespan of P388 tumor-bearing $B_6D_2F_1$ mice in a dose-dependent manner. This result is thought to be due to an immunosuppressive effect in vivo of the subject ardeemin derivatives.

TABLE 3

Survival Time Evaluation for BDF Mice Bearing P388/0 Tumors.[a]

| | Dose (mg/kg)[b] | | AWC (Gm) | | | | | SURVIVAL TIME[c] | | | | | | | |
|---|---|---|---|---|---|---|---|---|---|---|---|---|---|---|---|
| Cage (n) | Adr | 5NAcArd | D 0 | D 4 | D 6 | D 8 | D 11 | No. 1 | No. 2 | No. 3 | No. 4 | No. 5 | No. 6 | MST[d] | % ILS[e] |
| 1 (6) | — | — | 19.0 | +0.2 | +2.5 | +4.2 | — | 6.0 | 7.0 | 7.5 | 7.5 | 8.25 | 8.25 | 7.42 | 0 |
| 2 (4) | — | 3.33 | 19.4 | +0.9 | +3.3 | — | — | 6.0 | 7.0 | 8.0 | 8.0 | | | 7.25 | −2 |
| 3 (3) | — | 10 | 19.0 | +1.7 | +4.8 | — | — | 6.0 | 6.5 | 7.5 | | | | 6.67 | −10 |
| 4 (2) | — | 30 | 19.0 | +1.6 | +3.8 | — | — | 6.0 | 6.5 | | | | | 6.25 | −16 |
| 5 (4) | 0.333 | — | 19.5 | −0.1 | +0.5 | +1.4 | +3.5 | 12.25 | 13.0 | 14.25 | 15.5 | | | 13.75 | 85 |
| 6 (4) | 1.0 | — | 18.3 | −0.6 | −0.3 | +0.5 | +1.8 | 14.25 | 15.5 | 18.0 | 20.25 | | | 17.0 | 129 |
| 7 (4) | 3.0 | — | 18.5 | −1.2 | −1.0 | −0.8 | −0.1 | 16.0 | 17.25 | 19.25 | 20.25 | | | 18.19 | 145 |
| 8 (4) | 0.333 | 3.33 | 19.0 | −2.0 | −1.0 | +0.3 | +2.0 | 14.0 | 15.0 | 15.5 | 17.25 | | | 15.43 | 108 |
| 9 (3) | 1.0 | 10 | 19.0 | −2.0 | −1.1 | +0.1 | +1.7 | 16.0 | 16.0 | 18.0 | | | | 16.67 | 125 |
| 10 (2) | 3.0 | 30 | 20.0 | −2.7 | −2.5 | −2.0 | −1.8 | 18.0 | 21.0 | | | | | 19.5 | 163 |

[a]Male BDF mice were inoculated P388/0, $10^6$ cells/mouse, i.p. at Day 0, and treated by adriamycin and 5-N-acetyl-ardeemin starting Day 1 through Day 4, i.p. daily.
[b]Adr. = adriamycin, 5NAcArd. = 5-N-acetyl-ardeemin.
[c]Survival time were recorded based on the time of death with the following decimal values: 8 AM (0.0), 1 PM (0.25), 5 PM (0.5).
[d]MST = Mean survival time.
[e]% ILS = % increase in lifespan.

EXAMPLE 4

Immunosuppressive Effect in Heterotopic Mouse Cardiac Transplants (Prospective Example)

5-N-Acetylardeemin and 5-N-acetyl-8-desmethylardeemin are individually administered to mice which have received heterotopic cardiac transplants at a range of concentrations (40 mg/kg–1 mg/25 g per day), i.v., for seven days or fourteen days using an Alzet pump. Each compound is dissolved in DMSO at high concentration prior to administration. Control animals receive the same volume of carrier solvent (40 μL DMSO). The organ transplant in animals receiving an ardeemin derivative is found to be more resistant to graft rejection than the transplant in control mice which have not received the ardeemin derivative.

TABLE 4

Effects of 5-N-Ac-ardeemin (NAA), aspirin and hydrocortisone on inflammation induced by carrageene[a]

| Drug | Dose (mg/kg) | Route | Average Pedis Area (mm$^2$) Hours: | | | | | Toxicity | |
| --- | --- | --- | --- | --- | --- | --- | --- | --- | --- |
| | | | 0 | 12 | 24 | 48 | 60 | Death | n |
| Control | 0 | i.p. | 7.0 | 12.6 | 12.8 | 13.4 | 17.1 | 0/5 | 5 |
| NAA | 50 | i.p. | 6.8 | 12.4 | 12.7 | 11.3* | 15.6 | 0/5 | 5 |
| | 100 | i.p | 7.1 | 9.7*** | 9.0*** | 8.6*** | 10.2*** | 0/5 | 5 |
| Aspirin | 250 | p.o. | 6.9 | 12.5 | 12.3 | 13.2 | 15.4** | 0/5 | 5 |
| | 500 | p.o. | 6.8 | 9.9** | 10.6** | 9.0*** | 10.0*** | 0/5 | 5 |
| | 1000 | p.o. | 6.5 | 8.8*** | ND | ND | ND | 5/6 | 6 |
| Hydrocortisone | 1% Cream | Skin | 6.9 | 9.0*** | 8.9*** | 7.8*** | 7.9*** | 0/5 | 5 |

[a]0.75% carrogeene 40 μL was injected into mice pedis at 0.5 hr (i.v.) and 1.0 hr (p.o. and cream) before treatment. NAA was given at 0.5 hr before injection of carrageene and 12, 24 and 36 hrs after injection of carrageene. Aspirin and Hydrocortisone were given at 1 hr before injection of carrageene and 12, 24 and 36 hrs after injection of carrageene.
*P < 0.05,
**P < 0.01,
***P < 0.001 when compared with the corresponding controls.

What is claimed is:

1. A method for treating a subject in need of immunosuppression, comprising administering to the subject an effective amount of a compound having the structure:

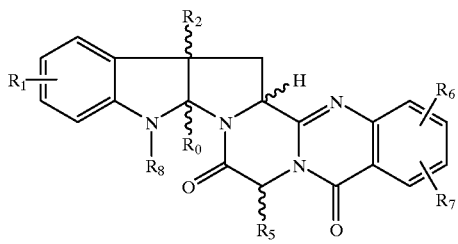

wherein $R_1$, $R_6$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, halophenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl, or $C_1$–$C_9$ linear or branched chain alkyl.

2. The method of claim 1 wherein the compound has the structure:

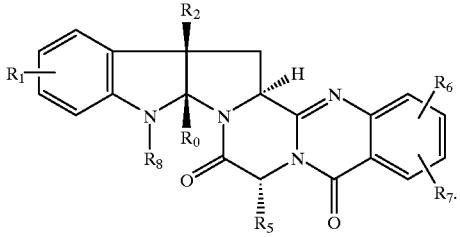

3. The method of claim 2 wherein $R_0$ is hydrogen.

4. The method of claim 1, wherein $R_0$, $R_1$, $R_3$, $R_4$, $R_6$, and $R_7$ are hydrogen; wherein $R_2$ is $CR_3R_3$—CH=$CHR_4$; wherein $R_5$ is H or $CH_3$; and wherein $R_8$ is —(C=O)$CH_3$.

5. A method for preventing organ graft rejection in a subject in whom an organ has been transplanted, comprising administering to the subject an effective amount of a compound having the structure:

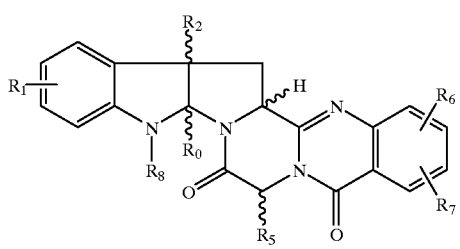

wherein $R_1$, $R_6$ and $R_7$ are independently hydrogen, OH, $NH_2$, SH, halogen, $C_1$–$C_9$ linear or branched chain alkyl, alkylmercapto, alkylamino, dialkylamino, alkoxy, phenyl, alkylphenyl, dialkylphenyl, halophenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —$CR_3R_3$—CH(O)$CH_2$, —$CR_3R_3$—$CH_2CH_3$, —$CR_3R_3$—$CH_2CH_2OH$, —$CR_3R_3$—CH(OH)$R_4$ or —$CR_3R_3$—CH=$CHR_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl, or $C_1$–$C_9$ linear or branched chain alkyl.

6. The method of claim 5 wherein the compound has the structure:

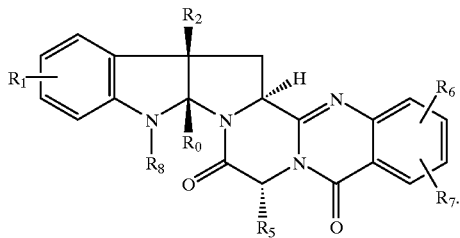

7. The method of claim 6 wherein $R_0$ is hydrogen.

8. The method of claim 5, wherein $R_0$, $R_1$, $R_3$, $R_4$, $R_6$, and $R_7$ are hydrogen; wherein $R_2$ is $CR_3R_3$—CH=CHR$_4$; wherein $R_5$ is H or $CH_3$; and wherein $R_8$ is —(C=O)CH$_3$.

9. The method of claim 5, wherein the organ is kidney, pancreas, liver, heart or bone marrow.

10. A method for treating a subject suffering from an autoimmune disease, comprising administering to the subject an effective amount of a compound having the structure:

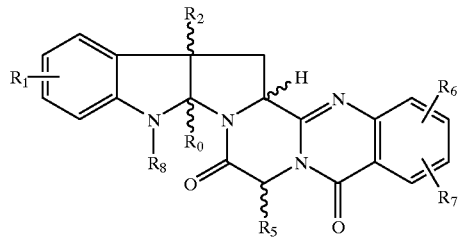

wherein $R_1$, $R_6$ and $R_7$ are independently hydrogen, OH, NH$_2$, SH, halogen, $C_1$–$C_9$ linear or branched chain alkyl, alkylmercapto, alkylamino, dialkylamino, alkoxy, phenyl, alkylphenyl, dialkylphenyl, halophenyl, alkoxyphenyl, hydroxyphenyl, benzyl, or hydroxybenzyl; wherein $R_0$, and $R_2$ are independently hydrogen, OH, $C_1$–$C_9$ linear or branched chain alkyl, —CR$_3$R$_3$—CH(O)CH$_2$, —CR$_3$R$_3$—CH$_2$CH$_3$, —CR$_3$R$_3$—CH$_2$CH$_2$OH, —CR$_3$R$_3$—CH(OH)R$_4$ or —CR$_3$R$_3$—CH=CHR$_4$; wherein $R_3$ and $R_4$ are independently hydrogen, halogen, $C_1$–$C_9$ linear or branched chain alkyl, phenyl, alkylphenyl, dialkylphenyl, alkoxyphenyl, or benzyl; wherein $R_5$ is hydrogen, $C_1$–$C_9$ linear or branched chain alkyl, phenyl, alkylphenyl, dialkylphenyl, alkoxyphenyl, benzyl, alkoxybenzyl, dialkoxybenzyl, indolylmethyl, alkylmercapto, or arylmercapto; and wherein $R_8$ is hydrogen, $C_1$–$C_9$ linear or branched chain acyl, benzoyl, alkylbenzoyl, dialkylbenzoyl, alkoxybenzoyl, benzyl, or $C_1$–$C_9$ linear or branched chain alkyl.

11. The method of claim 10 wherein the compound has the structure:

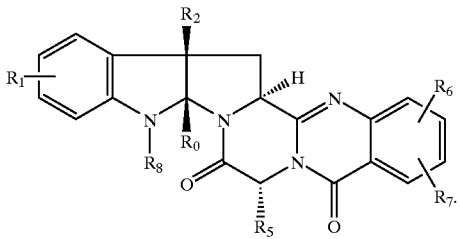

12. The method of claim 11 wherein $R_0$ is hydrogen.

13. The method of claim 10, wherein $R_0$, $R_1$, $R_3$, $R_4$, $R_6$, and $R_7$ are hydrogen; wherein $R_2$ is $CR_3R_3$—CH=CHR$_4$; wherein $R_5$ is H or $CH_3$; and wherein $R_8$ is —(C=O)CH$_3$.

14. The method of claim 10, wherein the disease is multiple sclerosis, rheumatoid arthritis, Crohn's disease or aplastic anemia.

* * * * *

UNITED STATES PATENT AND TRADEMARK OFFICE
CERTIFICATE OF CORRECTION

PATENT NO. : 6,355,639 B1
DATED : March 12, 2002
INVENTOR(S) : Chou et al.

It is certified that error appears in the above-identified patent and that said Letters Patent is hereby corrected as shown below:

Title page,
Item [73], Assignee, please add: -- Board of Regents, The University of Texas System, Austin, TX (US) --

Signed and Sealed this

Twenty-second Day of July, 2003

JAMES E. ROGAN
*Director of the United States Patent and Trademark Office*